(12) United States Patent
Tamura

(10) Patent No.: US 7,235,686 B2
(45) Date of Patent: Jun. 26, 2007

(54) PROCESS FOR PREPARING PHOSPHORIC ESTERS

(75) Inventor: Kazunari Tamura, Wanchai (HK)

(73) Assignee: Daihachi Chemical Industry Co., Ltd., Osaka (JP)

( * ) Notice: Subject to any disclaimer, the term of this patent is extended or adjusted under 35 U.S.C. 154(b) by 371 days.

(21) Appl. No.: 10/476,495

(22) PCT Filed: Apr. 25, 2002

(86) PCT No.: PCT/JP02/04189

§ 371 (c)(1),
(2), (4) Date: Aug. 10, 2004

(87) PCT Pub. No.: WO02/100868

PCT Pub. Date: Dec. 19, 2002

(65) Prior Publication Data

US 2004/0254390 A1    Dec. 16, 2004

(30) Foreign Application Priority Data

Jun. 8, 2001   (JP) ............................. 2001-174313
Sep. 11, 2001  (JP) ............................. 2001-275331

(51) Int. Cl.
*C07F 9/02* (2006.01)
(52) U.S. Cl. .................................................. 558/128
(58) Field of Classification Search ................ 558/128
See application file for complete search history.

(56) References Cited

U.S. PATENT DOCUMENTS

| 3,356,471 A | 12/1967 | Niedzielski |
| 4,442,239 A | 4/1984 | Tsunekawa et al. |
| 4,683,255 A | 7/1987 | Sugio et al. |
| 5,104,450 A | 4/1992 | Sand et al. |

FOREIGN PATENT DOCUMENTS

| GB | 2093458 | 9/1982 |
| JP | 49-19861 | 5/1974 |
| JP | 61-200163 | 9/1986 |
| JP | 2000-239286 | 9/2000 |
| WO | 92/05219 | 4/1992 |
| WO | 00/49024 | 8/2000 |

OTHER PUBLICATIONS

English Language Abstract of JP 61-200163, published Sep. 4, 1986.
English Language Abstract of JP 2000-239286, published Sep. 5, 2000.

*Primary Examiner*—Joseph K. McKane
*Assistant Examiner*—Robert Shiao
(74) *Attorney, Agent, or Firm*—Greenblum & Bernstein, P.L.C.

(57) ABSTRACT

A process for preparing a phosphoric ester, comprising: Step (1) of reacting naphthol with phosphorus oxychloride in a molar ratio of 1:1.3 or more in the presence of a metallic halide and removing unreacted phosphorus oxychloride and Step (2) of reacting the reaction product of Step (1) with phenol in a molar ratio (molar ratio of chlorine contained in the reaction product to phenol) of 1:1–1.5 and removing hydrogen chloride produced as a by-product to thereby obtain a phosphoric ester represented by the general formula (I):

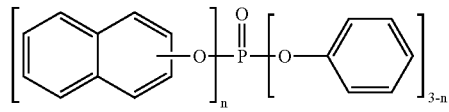

wherein n is 1 or 2.

20 Claims, No Drawings

PROCESS FOR PREPARING PHOSPHORIC ESTERS

This application is a 371 of PCT/JP02/04189 filed on Apr. 25, 2002,

1. Technical Field

The present invention relates to a process for preparing phosphoric esters. More particularly, the present invention relates to a process for preparing phosphoric esters in a solid form excellent in the ease of handling as a flame-retarder.

2. Background Art

As flame-retarders for resins, inorganic flame-retarders, organic halogen-containing flame-retarders and organophosphorus flame-retarders are known. In order to obtain sufficient flame retardancy by the inorganic flame-retarders, the flame-retarders need to be added to the resins in a large amount, and this addition in a large amount results in deterioration in the properties of the resins themselves. The organic halogen-containing flame-retarders are excellent in flame retardancy, but generate a hydrogen halide by pyrolysis when resin products are molded to cause corrosion of metal molds, and furthermore, generate toxic gases when burning, for example, in a fire to produce ill effect on humans. For the above reasons, attention has been paid to the organophosphorus flame retarders.

As the organophosphorus flame-retarders, monomeric type compounds such as triphenyl phosphate, tricresyl phosphate and the like are known. These compounds because they have low molecular weights have a drawback that they themselves volatilize when resin products are molded to contaminate dies so that the productivity of resin molds is decreased at the molding process.

In order to solve this problem, polymeric type condensed organophosphorus flame-retarders such as resorcin bis (diphenyl phosphate), bisphenol A bis(diphenyl phosphate) and the like have been developed. These compounds are capable of providing to resins flame retardancy equivalent to that given by the monomeric type organophosphorus flame-retarders, in addition to overcoming the above drawback of volatilization of monomers because they have high molecular weights. These compounds, however, are difficult to handle because they are highly viscous liquids, and, for this reason, for applying them uniformly onto resins, a heater for reducing their viscosity or a specific pump is required.

Furthermore, resorcin bis(diphenyl phosphate) is poor in hydrolysis, and decreases the durability of resin products. Also, bisphenol A bis(diphenyl phosphate) has a low phosphorus content in its molecule, and must be added in a large amount so that it produces flame retardancy.

Resorcin bis(di-2,6-xylyl phosphate) is commercially available as a low-volatile organophosphorus flame-retarder excellent in hydrolysis and easy to handle because it is in solid state in an working environment (at normal temperature) at the process of molding resins. However, this compound is expensive, and not suitable for general goods.

Japanese Unexamined Patent Publication No. SHO 61(1986)-200163 describes low-volatile naphthyl phosphate compounds as flame-retarders for polyphenylene ethers. This publication describes a method for obtaining a naphthyl phosphate compound by reacting 1 mole of 2-naphthol with 1 mole of phosphorus oxychloride in the presence of aluminum chloride and reacting the reaction product thus given with 2 moles of phenol. However, this publication does not discuss a technique of reacting excess phosphorus oxychloride and removing unreacted phosphorus oxychloride.

A naphthyl phosphate compound obtained by the method described in an example of the above publication comprises 7% by weight of triphenyl phosphate (TPP), 64% by weight of naphthyl diphenyl phosphate, 27% by weight of dinaphthyl phenyl phosphate and 2% by weight of trinaphthyl phosphate, is in a liquid state and therefore, is difficult to uniformly apply onto resins. The naphthyl phosphate compound, because it has a content of high volatile TPP as high as 7% by weight, does not satisfy a requirement of a flame-retarder that it must be low volatile. Also, in this example of the publication, the end reaction product is distilled in order to increase the content (purity) of 2-naphthyl diphenyl phosphate therein, and this distillation process serves to reduce the yield of the target compound.

As a method for synthesizing high-purity naphthyl diphenyl phosphate, a method is known comprising reacting diphenyl phosphorochloridate with naphthol in the presence of a Lewis acid catalyst. The diphenyl phosphorochloridate as a raw material for this reaction can be obtained by a reaction between phenol and phosphorus oxychloride, as described in, for example, Japanese Unexamined Patent Publication No. 2000-239286. In this reaction, however, the diphenyl phosphorochloridate cannot be synthesized selectively because triphenyl phosphate and monophenyl phosphorodichloridate are produced as by-products. Accordingly, purification by distillation of the reaction products is indispensable for the synthesis of the high-purity naphthyl diphenyl phosphate, while it serves to reduce the yield of the target compound.

Moreover, the above-reaction presents another problem of volatilization of the naphthol in association with the generation of hydrogen chloride to adhere to a reaction apparatus such as a condenser, a piping or the like or to produce a blockage in the apparatus. This problem is difficult to solve because 1-naphthol and 2-naphthol have melting points of 96° C. and 123° C., respectively, and naphthol is insoluble in a solvent such as toluene, xylene or o-dichlorobenzene used in the reaction. Also, there is still another problem of remaining of naphthol in the reaction product because naphthol has a boiling point higher than that of phenol so that it is difficult to remove the naphthol from the reaction product.

For solving the above problem, there is a measure to use a tertiary amine such as triethylamine a hydrogen chloride scavenger. This measure, however, requires the use of a large amount of reaction solvent and the recovery and purification of amine, and thus is not preferable in terms of production costs.

DISCLOSURE OF INVENTION

An object of the present invention is to provide a process for preparing phosphoric esters in a solid form excellent in the ease of handling as a flame-retarder.

According to the present invention, provided is a process for preparing a phosphoric ester, comprising:

Step (1) of reacting naphthol with phosphorus oxychloride in a molar ratio of 1:1.3 or more in the presence of a metallic halide and removing unreacted phosphorus oxychloride and Step (2) of reacting the reaction product of Step (1) with phenol in a molar ratio (molar ratio of chlorine contained in the reaction product to phenol) of 1:1–1.5 and removing hydrogen chloride produced as a by-product to thereby obtain a phosphoric ester represented by the general formula (I):

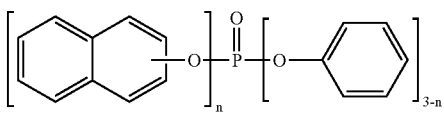

wherein n is 1 or 2.

MODE FOR CARRYING OUT THE INVENTION

According to the process of the present invention, provided is the phosphoric ester (I), i.e., a mixture of a compound of the general formula (I) wherein n=1 (naphthyl diphenyl phosphate) and a compound wherein n=2 (dinaphthyl phenyl phosphate). The ratio between the contents of these compounds varies depending on preparation conditions, and in the present phosphoric ester (I), the main component is the compound wherein n=1, i.e., naphthyl diphenyl phosphate. The present phosphate (I) may contain, as impurities, trace amounts of a compound wherein n=0 (triphenyl phosphate) and a compound wherein n=3 (trinaphthyl phosphate).

The present phosphate (I) has preferably a melting point of 50° C. or higher in order to satisfy the requirements for flame-retarders to be in a solid form easy to handle in working environment (at normal temperature) at the process of molding resins and to be low volatile.

The reactions in the process of the present invention proceed as follows:

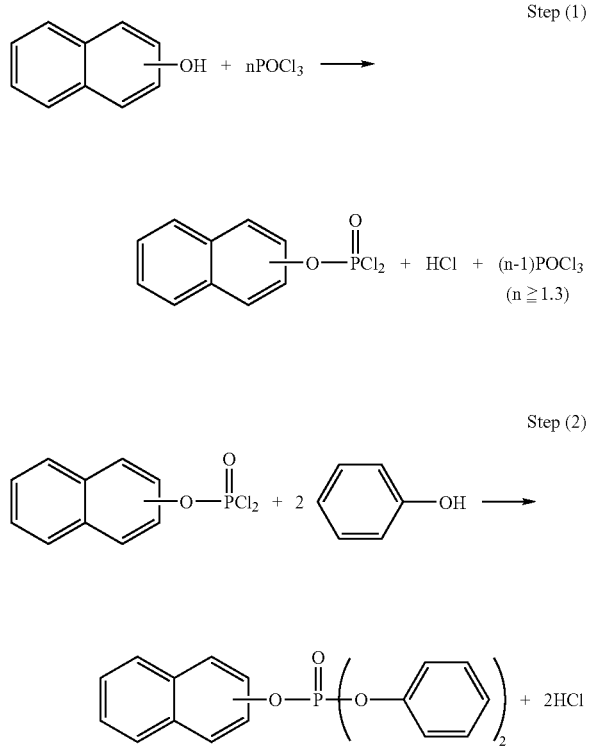

In Step (1), by reacting naphthol with phosphorus oxychloride in the molar ratio of 1:1.3 or more, mononaphthyl phoshorodichloridate and hydrogen chloride are produced while unreacted phosphorus oxychloride is left. Subsequently, the unreacted phosphorus oxychloride is removed by, for example, distillation. The hydrogen chloride produced (as a by-product) is preferably removed to the outside of the reaction system by a known method.

In the following Step (2), by reacting the obtained mononaphtyl phoshorodichloridate with phenol, naphthyl diphenyl phosphate and hydrogen chloride are produced. The hydrogen chloride produced (as a by-product) is removed by a known method.

The steps of the preparation process of the present invention will now be explained in detail.

The naphthol used in Step (1) of the present invention may be any of 1-naphthol, 2-naphthol and a mixture of these. However, 2-naphthol is particularly preferable because the obtained phosphoric ester (I) will have a high melting point and 2-naphthol is commercially available at a low cost. In other words, between 1-naphthyl diphenyl phosphate and 2-naphthyl diphenyl phosphate, with melting points of 52° C. and 63° C., respectively, the latter is preferable in consideration of the requirements to be in a solid form easy to handle in a working environment (at normal temperature) and to be low volatile.

The metallic halide used in Step (1) acts as a catalyst. Specific examples of the metallic halide include magnesium chloride, aluminum chloride, zinc chloride, titanium tetrachloride, boron trifluoride and the like. These metallic halides may be used in a combination of two or more. Among these, preferable are/is magnesium chloride and/or aluminum chloride and particularly preferable is magnesium chloride because it selectively induces generation of the mononaphthyl phosphorodichloridate.

The amount of the phosphorus oxychloride used in the reaction of Step (1) is 1.3 moles or more with respect to one mole of naphthol.

It is not preferable that the phosphorus oxychloride is used in less than 1.3 moles with respect to one mole of the naphthol. This is because the obtained phosphoric ester (I) will have a lower melting point, will be in a liquid state or in a sticky crystalline state in a working environment, and thereby, the ease of handling when it is added to resins as a flame-retarder will be impaired. However, as the ratio of the phosphorus oxychloride to be used is increased, the content of naphthyl diphenyl phosphate in the obtained phosphoric ester (I) becomes larger, while there is a larger amount of unreacted phosphorus oxychloride to be removed after the reaction. Accordingly, it is appropriate to use the phosphorus oxychloride in up to about 5 moles, and it is practical to use the phosphorus oxychloride in up to about 3 moles, with respect to one mole of naphthol.

In Step (1), an excess amount of phosphorus oxychloride is used with respect to the naphthol. This excess amount of phosphorus oxychloride serves also as a solvent, and therefore, no other reaction solvents are particularly needed. Further, because the naphthol is soluble in phosphorus oxychloride, there will be raised no such a problem of adherence of the naphthol to a reaction apparatus such as a reactor or a condenser.

The reaction temperature in Step (1) is preferably 70 to 150° C., and more preferably 80 to 120° C. It is not preferable that the reaction temperature is below 70° C. because the reactivity is decreased. Also, it is not preferable that the reaction temperature exceeds 150° C. because an ester exchange reaction occurs to decrease the content of the mononaphthyl phosphorodichloridate.

As the reaction time in Step (1), ordinarily, about 2 to 5 hours is sufficient though the reaction time may be varied depending on other conditions such as the reaction temperature.

The reaction in Step (1) is preferably carried out in an atmosphere of an inert gas such as a nitrogen gas for blocking moisture.

After the reaction in Step (1), unreacted phosphorus oxychloride is removed. Specifically, unreacted phosphorus oxychloride is removed conveniently as a low-boiling component through distillation under reduced pressure. The distillation under reduced pressure is preferably carried out at a temperature of about 100 to 150° C. and at a pressure of 10 kPa or lower (more preferably, under a reduced pressure of 5 to 1 kPa). The removed phosphorus oxychloride may be recovered and reused as it is as a raw material for the subsequent reaction. It is not preferable to leave phosphorus oxychloride in the reaction system because if phosphorus oxychloride is left, it reacts with phenol in Step (2) to produce high-volatile triphenyl phosphate.

The amount of the phenol in the reaction in Step (2), is 1 to 1.5 moles, and preferably 1.01 to 1.2 moles with respect to one mole of the reaction product (the amount of the phenol with respect to chlorine contained in the reaction product). In other words, assuming that the reaction product as a whole of Step (1) is mononaphthyl phoshorodichloridate, the phenol is used in 2 to 3 moles with respect to the reaction product of Step (1).

It is not preferable that phenol is used in less than 1 mole with respect to one mole of the reaction product of Step (1) because the reaction does not complete, and unreacted chlorine remains in the reaction product. Also, it is not preferable that the phenol is used in more than 1.5 moles with respect to one mole of the reaction product of Step (1) because a naphthyl group of the produced naphthyl diphenyl phosphate is substituted with a phenyl group to produce high-volatile triphenyl phosphate.

The chlorine content in the reaction product may be measured in the following manner, for example: The reaction solution in which phosphorus oxychloride has been already removed is dissolved in ethanol; to the resulting solution, sodium hydroxide or potassium hydroxid is added to render the solution alkaline; the resulting mixture is refluxed for 30 min. and cooled; and nitric acid is added to render the solution acidic, followed by titration with a silver nitrate solution.

The reaction temperature in Step (2) is preferably 100 to 200° C., and more preferably 110 to 160° C. It is not preferable that the reaction temperature is below 100° C. because the reactivity is decreased. Also, it is not preferable that the reaction temperature exceeds 200° C. because an ester exchange reaction occurs to produce high-volatile triphenyl phosphate.

As the reaction time in Step (2), ordinarily, about 3 to 8 hours is sufficient though the reaction time may be varied depending on other conditions such as the reaction temperature.

The reaction in Step (2) is preferably carried out in an atmosphere of an inert gas such as a nitrogen gas for the purpose of blocking moisture.

Also, in the reaction of Step (2), it is preferable to remove hydrogen chloride produced (as a by-product), by rendering the reaction system under reduced pressure or blowing an inert gas as nitrogen gas or the like into the reaction system.

In the reaction of Step (2), the problem tends to occur that phenol volatilizes to precipitate as crystals and to adhere to a reaction apparatus such as a reactor or a condenser, producing a blockage in the apparatus.

In order to solve this problem, it is preferable that the reaction in Step (2) is carried out with a solvent inert to the reaction, namely, while refluxing a solvent inert to the reaction. Examples of the solvents include toluene, xylene, chlorobenzene, o-dichlorobenzene and the like. The amount of the solvent to be used is about 5 to 20% by weight with respect to phenol.

Further, in order to solve the above problem, it is desirable to set the temperature of cooling water in the condenser to be not lower than the melting point of phenol (about 41° C.) and provide a second condenser for scavenging phenol.

The reaction product in Step (2) can be used as it is as a flame-retarder for resins by removing the solvent or low boiling point components such as excess (unreacted) phenol by a known method such as distillation under reduced pressure.

Further, by using a high-vacuum apparatus, the product can be taken out by distilling. In such a case, a post-processing to be mentioned later is not needed.

Examples of the distillation under reduced pressure for removing low boiling point components include steam distillation under a reduced pressure of not higher than 8 kPa at a temperature of about 120 to 160° C., for example.

Before the distillation under reduced pressure, the obtained reaction mixture may be washed with water or with a solvent such as toluene, xylene, chlorobenzene, o-dichlorobenzene or the like. The temperatures of the water for washing and the reaction mixture are preferably about 70 to 90° C. in order to prevent the reaction product from precipitating as crystals.

Moreover, the reaction product obtained may be recrystallized using a mixed solvent such as methanol-water, ethanol-water or the like.

Metallic components or acidic components which may be derived from naphthol, phosphorus oxychloride and phenol used as the raw material, from a metallic halide used as the catalyst and from a solvent and which remain in the reaction product are preferably removed by a known method if they cause an adverse effect on the properties of the resin composition containing the reaction product as a flame-retarder. Examples of the removing method include washing with an aqueous acid solution, washing with an aqueous alkali solution, washing with water, distillation under reduced pressure, recrystallization and the like.

With the washing with an aqueous acid solution, the metallic components in the reaction product can be removed. Specifically, the metallic components can be removed by washing the obtained reaction product with an aqueous acid solution such as an aqueous solution of hydrochloric acid, sulfuric acid, phosphoric acid, nitric acid, oxalic acid, citric acid or the like (for example, a 3.5% aqueous solution of hydrochloric acid).

With the washing with an aqueous alkali solution, the acidic components in the reaction product can be removed. Specifically, the acidic components can be removed by washing the obtained reaction product with an aqueous alkali solution such as an aqueous solution of sodium hydroxide, potassium hydroxide, calcium hydroxide, sodium carbonate, sodium bicarbonate or the like (for example, a 1% aqueous solution of sodium hydroxide).

The phosphoric ester (I) prepared according to the process of the present invention can be used as an inexpensive non-halogen flame-retarder low-volatile and excellent in resistance to hydrolysis which provides in a small amount excellent flame retardancy to resins without decreasing the intrinsic mechanical strength thereof. This flame-retarder can be used as one effective for both thermoplastic resins and thermosetting resins.

Examples of the thermoplastic resins include poly(phenylene ether) (for example, modified polyphenyleneether (modified PPE)), polyethylene, polypropylene, polystyrene, impact-resistant polystyrene, ACS resin, AS resin, ABS resin (ABS), polycarbonate (PC), polyamide, polyimide, poly(methyl methacrylate), poly(phenylene sulfide), polyether ether ketone, polyether sulfone, polysulfone, polyarylate, poly(ethylene terephthalate) (PET), poly(butylene terephthalate) (PBT), poly(butylene naphthalate) (PEN), polyacetal, polyether ketones, polyether nitrile, polythioether sulfone, polybenzimidazole, polycarbodiimide and liquid crystalline polymer, as well as polymer blends and polymer alloys (for example, PC/ABS polymer alloy) of these.

Examples of the thermosetting resins include polyurethane, phenolic resin, melamine resin, urea resin, epoxy resin, unsaturated polyester, diallyl phthalate resin, as well as polymer blends and polymer alloys of these.

The amount of the phosphoric ester (I) to be added according to the present invention is properly determined depending on the kind of resins to which the phosphoric ester (I) is to provide flame retardancy and depending on the required degree of the flame retardancy, but is usually about 1 to 100 parts by weight with respect to 100 parts by weight of the resin.

A flame retarded resin composition can be obtained by adding to the above-mentioned resin the phosphoric ester (I) prepared according to the process of the present invention together with various additives generally added to resin compositions and mixing and melt-kneading the resulting mixture by a known method.

Examples of the additives include flame-retarders other than the phosphoric ester (I) of the present invention, flame-retardant auxiliaries, agents for preventing dripping, fillers, antioxidants (stabilizers), antistatic agents, lubricants (softeners), pigments, ultraviolet light absorbers (light stabilizers), reinforcements and the like.

A mold with a desired shape can be obtained by molding the obtained resin composition by a known method.

EXAMPLES

The present invention will be explained in detail by way of the following examples, comparative examples, test examples and comparative test example, which should not be construed to limit the scope of the invention.

Example 1

Into a one-liter four-necked flask provided with a stirrer, a condenser and a thermometer, 144.2 g (1 mole) of 2-naphthol, 199.4 g (1.3 moles) of phosphorus oxychloride and 0.5 g of anhydrous magnesium chloride were fed. Then, the resulting mixed solution was heated with stirring in nitrogen atmosphere to 120° C. in an hour, and then reacted by stirring at the same temperature (120° C.) for an hour. After the reaction, the pressure was reduced to about 1.5 kPa while maintaining the solution at 120° C. to recover excess (unreacted) phosphorus oxychloride.

Subsequently, the reaction mixture was cooled to room temperature, and then 188.0 g (2 moles) of phenol (equivalent to 1.14 moles with respect to one mole of chlorine existing in the reaction product) and 10 g of toluene were added. The resulting mixed solution was heated with stirring in nitrogen atmosphere to 160° C. in 2 hours, and then reacted for 3 hours while refluxing toluene under a reduced pressure (about 20 kPa) at the same temperature (160° C.).

The reaction solution was cooled to 80° C., nitrogen was introduced into the flask to set the pressure inside the flask to an atmospheric pressure, and the reaction solution was washed with a 3.5% aqueous solution of hydrochloric acid and a 1% aqueous solution of sodium hydroxide successively and finally with water at the same temperature (80° C.). Further, the resulting solution was steam distilled under a reduced pressure (about 2.7 kPa) at 150° C. to remove low boiling point components from the reaction product, thereby obtaining 344 g of a pale brownish solid. Assuming that the solid as a whole was the target compound, the rough yield of the product was 91%.

The composition of the obtained product was determined from area percentages of components appearing in liquid chromatography carried out under the following conditions.

Column: ODS-80TM manufactured by Tosoh Corporation in Japan
Elute: 90% by volume of methanol/10% by volume of water
Wavelength of a Detector: 254 nm Also, the melting point of the product was measured as a temperature reached when the product completely melted.

The results of the liquid chromatography are shown in Table 1 together with the metallic halide and the molar ratio of phosphorus oxychloride to naphthol used.

Example 2

A pale brownish solid of 360 g was obtained in the same manner as in Example 1 except that 306.7 g (2.0 moles) of phosphorus oxychloride was used. Assuming that the solid as a whole was the target compound, the rough yield of the product was 96%. The phenol of 2 moles used in the Step (2) was equivalent to 1.06 moles with respect to one mole of chlorine existing in the reaction product in Step (1).

The composition and melting point of the obtained product were determined in the same manner as in Example 1.

The results are shown in Table 1 together with the metallic halide and the molar ratio of phosphorus oxychloride to naphthol used.

Example 3

A pale brownish solid of 361 g was obtained in the same manner as in Example 1 except that 460.1 g (3.0 moles) of phosphorus oxychloride was used. Assuming that the solid as a whole was the target compound, the rough yield of the product was 96%. The phenol of 2 moles used in the Step (2) was equivalent to 1.04 moles with respect to one mole of chlorine existing in the reaction product in Step (1).

The composition and melting point of the obtained product were determined in the same manner as in Example 1.

The results are shown in Table 1 together with the metallic halide and the molar ratio of phosphorus oxychloride to naphthol used.

Example 4

A pale brownish solid of 346 g was obtained in the same manner as in Example 1 except that 0.5 g of anhydrous aluminum chloride was used in place of 0.5 g of anhydrous magnesium chloride. Assuming that the solid as a whole was the target compound, the rough yield of the product was 92%. The phenol of 2 moles used in the Step (2) was equivalent to 1.11 moles with respect to one mole of chlorine existing in the reaction product in Step (1).

The composition and melting point of the obtained product were determined in the same manner as in Example 1.

The results are shown in Table 1 together with the metallic halide and the molar ratio of phosphorus oxychloride to naphthol used.

Comparative Example 1

A pale brownish sticky solid of 341 g was obtained in the same manner as in Example 1 except that 168.7 g (1.1 moles) of phosphorus oxychloride was used. Assuming that the solid as a whole was the target compound, the rough yield of the product was 91%. The phenol of 2 moles used in the Step (2) was equivalent to 1.15 moles with respect to one mole of chlorine existing in the reaction product.

The composition and melting point of the obtained product were determined in the same manner as in Example 1.

The results are shown in Table 1 together with the metallic halide and the molar ratio of phosphorus oxychloride to naphthol used.

Comparative Example 2

(Retest of Reference Example 1 in Japanese Unexamined Patent Publication No. SHO 61(1986)-200163)

Into a two-liter four-necked flask provided with a stirrer, a condenser and a thermometer, 289.0 g (2 moles) of 2-naphthol, 307.0 g (2 moles) of phosphorus oxychloride and 3.0 g of anhydrous aluminum chloride were fed. Then, the mixed solution was heated with stirring in a nitrogen atmosphere to 150° C. in 5 hours. Then, the resulting mixture was further heated to 165° C. in 3 hours to be reacted.

Subsequently, the reaction solution was cooled to room temperature, and then 376.0 g (4 moles) of phenol was added. The resulting mixed solution was heated with stirring in a nitrogen atmosphere to 190° C. in 6 hours, and then reacted by heating to 200° C. in 3 hours.

The reaction solution was cooled and dissolved in the substantially same volume of carbon tetrachloride, and the resulting solution was washed with shaking with a 3% aqueous solution of sodium chloride three times and finally with water. Then, the carbon tetrachloride was distilled off under reduced pressure, and the solution was further distilled under a reduced pressure (about 70 kPa) to remove distillate whose boiling point is up to 180° C., thereby obtaining 719 g of a pale brownish liquid. Assuming that the solid as a whole was the target compound, the rough yield of the product was 96%.

The composition of the product obtained was determined in the same manner as in Example 1.

The results are shown in Table 1 together with the metallic halide and the molar ratio of phosphorus oxychloride to naphthol used.

Comparative Example 3

A pale brownish liquid of 457 g was obtained in the same manner as in Example 1 except that unreacted phosphorus oxychloride was not recovered and that 272.9 g (2.9 moles) of phenol (equivalent to 1 mole with respect to one mole of chlorine existing in the reaction product) was used. The rough yield of the product was 96%, assuming that the liquid was a mixture of 0.3 moles of triphenyl phosphate and 1 mole of naphthyl diphenyl phosphate.

The composition of the obtained product was determined in the same manner as in Example 1.

The results are shown in Table 1 together with the metallic halide and the molar ratio of phosphorus oxychloride to naphthol used.

TABLE 1

|  | Example 1 | Example 2 | Example 3 | Example 4 | Comp. Ex. 1 | Comp. Ex. 2 | Comp. Ex. 3 |
|---|---|---|---|---|---|---|---|
| Molar Ratio | 1.3 | 2.0 | 3.0 | 2.0 | 1.1 | 1.0 | 1.3 |
| Catalyst | $MgCl_2$ | $MgCl_2$ | $MgCl_2$ | $AlCl_3$ | $MgCl_2$ | $AlCl_3$ | $MgCl_2$ |
| Composition (%) |  |  |  |  |  |  |  |
| TPP | 0.7 | 0.3 | 0.6 | 0.7 | 0.7 | 4.1 | 6.6 |
| NDPP | 85.5 | 92.6 | 95.2 | 86.5 | 79.0 | 60.4 | 80.8 |
| DNPP | 13.7 | 7.1 | 4.3 | 12.7 | 20.1 | 33.5 | 12.5 |
| TNP | 0.1 | nd | nd | 1.0 | 0.2 | 2.0 | 0.1 |
| Melting Point (° C.) | 61 | 61 | 63 | 61 | 58 | Liquid | Liquid |

Molar ratio: phosphorus oxychloride/2-naphthol
Catalyst: metallic halide used
TPP: triphenyl phosphate
NDPP: naphthyl diphenyl phosphate
DNPP: dinaphthyl phenyl phosphate
TNP: trinaphthyl phosphate The results in Table 1 show that the products of Examples 1 to 4 are solids with melting points within the range 61 to 63° C. each comprising 85 to 95% of NDPP as a main component and 1% or less of high volatile TPP. Thus, it is shown that, according to the preparation process of the present invention, it is possible to prepare a phosphoric ester in a solid form excellent in the ease of handling as a flame-retarder.

The products of Comparative Examples 1 to 3 not through the preparation process of the present invention, on the other hand, are solids or liquids sticky at room temperature and interior in the ease of handling as a flame-retarder.

Test Example 1

The phosphoric ester of 16 parts by weight obtained in Example 1 as a flame-retarder and 0.4 parts by weight of poly(tetrafluoro ethylene) (PTFE manufactured by DU PONT-MITSUI FLUOROCHEMICALS CO., LTD., in Japan, trade name: PTFE 6-J) as an agent for preventing dripping were mixed with 100 parts by weight of a PC/ABS polymer alloy (manufactured by Daicel Chemical Industries, Ltd. in Japan, trade name: Novalloy S1500) in a Henschel mixer and were melt-kneaded in a vent-type twin-screw extruder to produce resin compositions in pellets. These obtained pellets were molded in an injection molding machine to give samples for flame retardancy (perpendicular flammability) test, which were then evaluated by the following method.

The results are shown in Table 2 together with the components of the resin composition and the blending ratio thereof.

(1) Perpendicular Flammability (UL) Test
   Test Method
      according to UL-94 (mean time of 5 samples to extinction of fire)
   Sample: 1.6 mm thick
   Evaluation
      : defined ranks V-0, V-1 and V-2
(2) Loss in Weight on Heating A measurement was made of the losses in weight (% by weight) of the resin compositions in pellets (diameter: about 3 mm, length: about 3 mm, weight: about 10 mg) when the resin compositions in pellets were heated to 250° C. at a temperature-rising rate of 20° C./min. in an open cell by a thermobalance in a nitrogen atmosphere.

Example 1, however, is a solid, and thus is excellent in the ease of handling as a flame-retarder when compared with the liquid phosphoric ester obtained in Comparative Example 3.

Test Example 2 and Comparative Test Example 2

A measurement was made of the losses in weight on heating of the phosphoric esters themselves obtained in Example 1 and in Comparative Example 3, respectively. That is, a measurement was made of the losses in weight when the phosphoric esters were heated to 250° C. and 300° C. at a temperature-rising rate of 10° C./min. in an open cell by a thermobalance in a nitrogen atmosphere.

The results are shown in Table 3.

TABLE 3

|  |  | Test Example 2 | Comp. Test Ex. 2 |
|---|---|---|---|
| Composition as Flame-Retarder |  | Example 1 | Comp. Ex. 3 |
| Loss in Weight | 250° C. | 0.7 | 4.1 |
| on heating | 300° C. | 5.6 | 18.4 |
| (% by weight) |  |  |  |

There was a considerable amount of smoke when the samples for flame retardancy were produced using the phosphoric ester obtained in Comparative Example 3. This phenomenon is considered to be attributed to evaporation of high volatile TPP contained in the phosphoric ester due to generation of heat at the molding of the samples. This evaporation of TPP, which causes contamination of molding dies, can be expected from the values of the losses in weight on heating of the resin compositions in Table 2 and of the phosphoric esters themselves in Table 3. As seen, the phosphoric ester of Comparative Example 3 and the resin composition containing it incur larger loss in weight on heating than the phosphoric ester of Example 1 and the resin composition containing it.

TABLE 2

|  |  |  | Test Example 1 | Comp. Test Ex. 1 |
|---|---|---|---|---|
| Composition (part by weight) | Resin Component | PC/ABS | 100 | 100 |
|  | Component as Flame-Retarder | Example 1 | 16 | — |
|  |  | Comp. Ex. 3 | — | 16 |
|  | Agent for Preventing Dripping | PTFE | 0.4 | 0.4 |
| Properties | UL-94 | Rank | V-0 | V-0 |
|  | Loss in Weight on Heating | % by Weight | 0.6 | 1.1 |

Comparative Test Example 1

Samples for flame retardancy (perpendicular flammability) test were produced and evaluated in the same manner as in Test Example 1 except that the phosphoric ester obtained as a flame-retarder in Comparative Example 3 was used.

The results are shown in Table 2 together with the components of the resin composition and the blending ratio thereof.

The results in Table 2 show that the phosphoric ester obtained in Example 1 and the phosphoric ester in Comparative Example 3 can provide the same level of flame-retardancy to resins. The phosphoric ester obtained in Accordingly, the phosphoric ester of Example 1 obtained by the preparation process of the present invention is remarkably superior to the phosphoric ester of Comparative Example 3 in that it incurs small loss in weight on heating and has no risk of contaminating dies at the molding process and of aggravating a working environment.

An object of the present invention is to provide a process for preparing a phosphoric ester in a solid form excellent in the ease of handling as a flame-retarder.

The phosphoric ester prepared according to the process of the present invention can be used as an inexpensive non-halogen flame-retarder low-volatile and excellent in resistance to hydrolysis which provides in a small amount excellent flame retardancy to resins without decreasing the intrinsic mechanical strength thereof.

The invention claimed is:

1. A process for preparing a phosphoric ester, comprising:
Step (1) of reacting naphthol with phosphorus oxychloride in a molar ratio of 1:1.3 or more in the presence of a metallic halide and removing unreacted phosphorus oxychloride and
Step (2) of reacting the reaction product of Step (1) with phenol in a molar ratio (molar ratio of chlorine contained in the reaction product to phenol) of 1:1–1.5 and removing hydrogen chloride produced as a by-product to thereby obtain a phosphoric ester represented by the general formula (I):

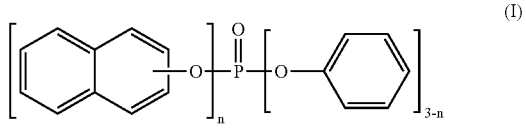

wherein n is 1 or 2.

2. The process for preparing a phosphoric ester of claim 1, wherein the metallic halide in Step (1) is magnesium chloride and/or aluminum chloride.

3. The process for preparing a phosphoric ester of claim 1, wherein the naphthol in Step (1) is 2-naphthol.

4. The process for preparing a phosphoric ester of claim 1, wherein the reaction in Step (1) is carried out at a reaction temperature of 70 to 150° C.

5. The process for preparing a phosphoric ester of claim 1, wherein the removal of the unreacted phosphorus oxychloride in Step (1) is carried out under a reduced pressure of 10 kPa or lower at a temperature of 100 to 150° C.

6. The process for preparing a phosphoric ester of claim 1, wherein the reaction product in Step (1) and phenol are reacted in a molar ratio (molar ratio of chlorine contained in the reaction product to the phenol) of 1:1.01–1.2 in Step (2).

7. The process for preparing a phosphoric ester of claim 1, wherein the reacting of Step (2) is carried out with solvent, and 5 to 20% by weight of the solvent is used with respect to phenol, the solvent being selected from toluene, xylene, chlorobenzene and o-dichlorobenzene.

8. The process for preparing a phosphoric ester of claim 1, wherein the reaction in Step (2) is carried out at a reaction temperature of 100 to 200° C.

9. The process for preparing a phosphoric ester of claim 1, wherein low boiling point components in the obtained phosphoric ester are removed under a reduced pressure of 8 kPa or lower at a temperature of 120 to 160° C.

10. The process for preparing a phosphoric ester of claim 1, wherein the obtained phosphoric ester is subjected to washing with an aqueous acid solution, washing with an aqueous alkali solution, washing with water, distillation under reduced pressure and, upon necessity, recrystallization to remove metallic components or acidic components derived from a raw material and remaining in the phosphoric ester.

11. The process for preparing a phosphoric ester of claim 1, wherein the phosphoric ester (I) of the general formula (I) has a melting point of at least 50° C.

12. The process for preparing a phosphoric ester of claim 2, wherein the naphthol in Step (1) is 2-naphthol.

13. The process for preparing a phosphoric ester of claim 2, wherein the reaction in Step (1) is carried out at a reaction temperature of 70 to 150° C.

14. The process for preparing a phosphoric ester of claim 3, wherein the reaction in Step (1) is carried out at a reaction temperature of 70 to 150° C.

15. The process for preparing a phosphoric ester of claim 2, wherein the removal of the unreacted phosphorus oxychloride in Step (1) is carried out under a reduced pressure of 10 kPa or lower at a temperature of 100 to 150° C.

16. The process for preparing a phosphoric ester of claim 3, wherein the removal of the unreacted phosphorus oxychloride in Step (1) is carried out under a reduced pressure of 10 kPa or lower at a temperature of 100 to 150° C.

17. The process for preparing a phosphoric ester of claim 2, wherein the reaction product in Step (1) and phenol are reacted in a molar ratio (molar ratio of chlorine contained in the reaction product to the phenol) of 1:1.01–1.2 in Step (2).

18. The process for preparing a phosphoric ester of claim 3, wherein the reaction product in Step (1) and phenol are reacted in a molar ratio (molar ratio of chlorine contained in the reaction product to the phenol) of 1:1.01–1.2 in Step (2).

19. The process for preparing a phosphoric ester of claim 4, wherein the reaction product in Step (1) and phenol are reacted in a molar ratio (molar ratio of chlorine contained in the reaction product to the phenol) of 1:1.01–1.2 in Step (2).

20. The process for preparing a phosphoric ester of claim 5, wherein the reaction product in Step (1) and phenol are reacted in a molar ratio (molar ratio of chlorine contained in the reaction product to the phenol) of 1:1.01–1.2 in Step (2).

* * * * *